United States Patent [19]
Lumma et al.

[11] Patent Number: 5,510,369
[45] Date of Patent: Apr. 23, 1996

[54] PYRROLIDINE THROMBIN INHIBITORS

[75] Inventors: William C. Lumma, Pennsburg; Roger M. Freidinger, Lansdale; Stephen F. Brady; Philip E. Sanderson, both of Philadelphia; Dong-Mei Feng, Harleysville; Terry A. Lyle, Lederach; Kenneth J. Stauffer, Pottstown; Thomas J. Tucker, North Wales; Joseph P. Vacca, Telford, all of Pa.

[73] Assignee: Merck & Co., Inc., Rahway, N.J.

[21] Appl. No.: 279,460

[22] Filed: Jul. 22, 1994

[51] Int. Cl.$^6$ .................. A61K 31/40; C07D 207/06
[52] U.S. Cl. .................. 514/422; 514/423; 548/518; 548/528; 548/537
[58] Field of Search .................. 548/537, 518, 548/528; 514/422, 423

[56] References Cited

FOREIGN PATENT DOCUMENTS

| | | |
|---|---|---|
| 52881/86 | 1/1986 | Australia. |
| 0363284A2 | 4/1990 | European Pat. Off.. |
| 0471651A2 | 2/1992 | European Pat. Off.. |
| 0479489A2 | 4/1992 | European Pat. Off.. |
| 601459A2 | 6/1994 | European Pat. Off.. |
| 603112A1 | 6/1994 | European Pat. Off.. |
| 0648780A1 | 4/1995 | European Pat. Off.. |
| 92/14750 | 3/1992 | WIPO. |
| WO92/07869 | 5/1992 | WIPO. |

OTHER PUBLICATIONS

Balasubramanian, et al. J. Med. Chem. Mar. 1993, 36, No. 2, pp. 300–303.
Shuman et al. J. Med. Chem. (8) 1993, 36, No. 3, pp. 314–319.
Kettner et al. The Journal of Biol. Chem., vol. 265, No. 30, Issue of 10/25; pp. 18289–18297 Oct. 1990.
J. Biol. Chemistry, Platelet Glycocalicin vol. 263, No. 10, pp. 3435–3443, T. Okumura et al. May 1978.
J. of Biol. Chem., The Binding of Thrombin to the Surface of Human Platelets, vol. 249, No. 8 pp. 2646–2651, Apr. 1974, Tollefsen et al.
Cell., Molecular Cloning of a Functional Thrombin . . . , vol. 64, pp. 1057–1068, Mar. 22, 1991, Thien–Khai H. Vu et al.
J. of Biol. Chemistry, Thrombin Interaction with Platelets, vol. 262, No. 7 pp. 3030–3036, Mar. (1987), Gronke et al.
J. of Biol. Chem., Structure–Function Relations in the Interaction of alpha–Thrombin with Blood Platelets, vol. 252, No. 20, 7118–7123 Oct. (1977), Workman et al.
Biochemical & Biophysical Research Commun., Minimal Sequence Requirement of Thrombin Receptor Agonist Peptide, vol. 184, No. 2 pp. 790–796 Apr. (1992), Kwan Y. Hui et al.

J. of Biol. Chem., Communication, vol. 267, No. 19, Jul. 1992, pp. 13146–13149, Scarborough et al.
J. of Biol. Chem., Structure–Function Relationships in the Activation of Platelet Thrombin Receptors by Receptor–derived Peptides*, vol. 267, No. 9, pp. 6081–6085 Mar. 1992, Vassallo et al.
Organic & Medicinal Chemistry Letters, alpha–Hydroxy- and alpha–Ketoester Functionalized Thrombin Inhibitors, vol. 2, No. 12, pp. 1607–1612, Iwanowicz et al. (8) 1992.
J. Am. Chem. Soc., Design, Synthesis and Kinetic Evaluation of a Unique Cladd of Elastase Inhibitors . . . , 114, 1854–1863, Edwards et al. (8) 1992.
Thrombos, Diathes, haemorrh. (Stuttg.), Thrombin Interaction with Human Platelets (8) 1974, 32, 207, David R. Phillips.
Chapter 3, Dept. of Biochemistry, St. Jude Children's Research Hospital, Platelet membrane proteins:composition and receptor function, Berndt and Phillips (8) 1981.
Biochemistry, Platelet Stimulation by Thrombin and Other Proteases, vol. 14, No. 6, (8) 1975, Martin et al.
Blood, PPack–Thrombin Inhibits Thrombin–Induced Platelet Aggregation . . . vol. 75, No. 10 May 1990, pp. 1983–1990, Greco et al.
The Embo Journal, The refined 1.9 A crystal structure of human alpha–thrombin . . . , vol. 8, No. 11 pp. 3467–3475, Bode et al. (8) 1989.
Tips vol. 14, Oct. 1993 Tapparelli et al.
Peptides, vol. 12, pp. 1153–1154, Anticoagulant Activity of a Peptide Boronic . . . Hussain et al. (8) 1991.

*Primary Examiner*—Johann Richter
*Assistant Examiner*—Laura L. Stockton
*Attorney, Agent, or Firm*—Richard S. Parr; Melvin Winokur

[57] ABSTRACT

Compounds of the invention have the following structure:

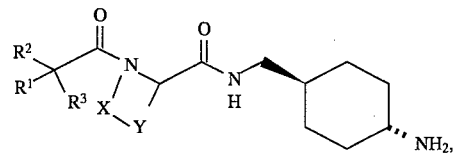

for example

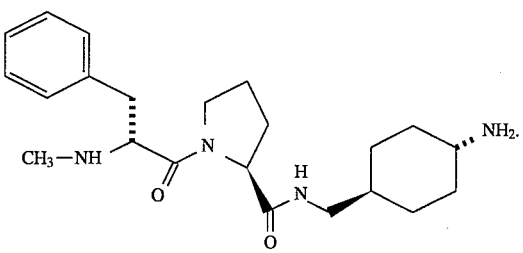

These compounds inhibit thrombin and associated thrombosis.

5 Claims, No Drawings

PYRROLIDINE THROMBIN INHIBITORS

BACKGROUND OF THE INVENTION

Thrombin is a serine protease present in blood plasma in the form of a precursor, prothrombin. Thrombin plays a central role in the mechanism of blood coagulation by convening the solution plasma protein, fibrinogen, into insoluble fibrin.

Edwards et al. *J. Amer. Chem. Soc.* (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

SUMMARY OF THE INVENTION

These compounds show selectivity for thrombin over trypsin and other trypsin-like enzymes and have oral bioavailability. Trypsin-like enzymes (such as trypsin, thrombin, factor xa, kallikrein, plasmin, urokinase, and plasminogen activator) are serine dependent enzymes that catalyze hydrolysis at arginyl and lysyl peptide bonds.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Some abbreviations that may appear in this application are as follows.

ABBREVIATIONS

| Designation | Protecting Group |
|---|---|
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT (HOBT or HOBt) | 1-hydroxybenzotriazole hydrate |
| Designation | Coupling Reagent |
| BOP reagent | benzotriazol-1-yloxytris-(dimethylainino)phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| | Other |
| (BOC)$_2$O(BOC$_2$O) | di-t-butyl dicarbonate |
| n-Bu$_4$N+F— | tetrabutyl ammonium fluoride |
| nBuLi (n-Buli) | n-butyllithium |
| DMF | dimethylformamide |
| Et$_3$N | triethylamine |
| EtOAc | ethyl acetate |
| TFA | trifluoroacetic acid |
| DMAP | dimethylaminopyridine |
| DME | dimethoxyethane |
| LDA | lithium diisopropylamide |
| THF | tetrahydrofuran |
| | Amino Acid |
| Ile | Isoleucine |
| Phe | Phenylalanine |
| Pro | Proline |
| Ala | Alanine |
| Val | Valine |

DETAILED DESCRIPTION OF THE INVENTION

Compounds of the invention have the following structure:

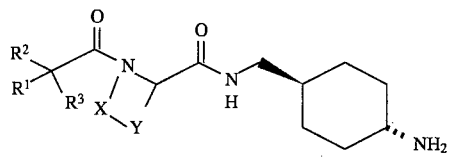

wherein
R$^1$ and R$^2$ are independently
  hydrogen,
  phenyl,
  mono- or di-halogenated phenyl,
  naphthyl,
  biphenyl,
a 5- to 7- membered mono- or bicyclic heterocyclic ring or bicyclic heterocyclic ring system any ring of which may be saturated or unsaturated, and which consists of carbon atoms and from one to three heteroatoms selected from the group consisting of N, O and S,
  C$_{1-4}$ alkyl,
  branched C$_{1-4}$ alkyl,
  C$_{3-7}$ cycloalkyl,
  C$_{5-12}$ bicylic alkyl,
  C$_{11-16}$ tricylic alkyl, $(CH_2)_n R^4$, $CH(R^4)_2$, wherein $R^4$ is the same or different, $CH(R^4)(OR^4)$, $(CH_2)_2 OR^4$, or $R^2$ may be joined with $R^1$ to form a four- to seven membered carbon ring in which zero to two carbon atoms may be substituted with heteroatoms independently selected from the list N, O, and S, where n is 1, 2, 3 or 4;

$R^3$ is

H, $N(R^1)_2$, wherein $R^1$ is the same or different, $R^1 OCONH$, $R^1 CONH$, $(CH_2)_p OH$, where p is 0, 1, 2, 3 or 4, $R^1 SO_2 NH$, or $(R^1)_m NCONH$, where m is 1 or 2, wherein $R^1$ is the same or different;

$R^4$ is phenyl, mono- or di-halogenated phenyl, naphthyl, biphenyl, a 5- to 7- membered mono- or bicyclic heterocyclic ring or bicyclic heterocyclic ring system any ring of which may be saturated or unsaturated, and which consists of carbon atoms and from one to three heteroatoms selected from the group consisting of N, O and S, $C_{1-4}$ alkyl, branched $C_{1-4}$ alkyl, $C_{3-7}$ cycloalkyl, $C_{5-12}$ bicyclic alkyl, or $C_{11-16}$ tricyclic alkyl;

X is $(CH_2)_q$ where q is 1 or 2; or $NR_1 CH_2$; and

Y is $SCH_2$, or $(CH_2)_r$ where r is 1 or 2.

In one class of compounds of the invention, X is $(CH_2)_q$; q is 1; Y is $(CH_2)_r$; and r is 1 or 2. Specific embodiments of this class include

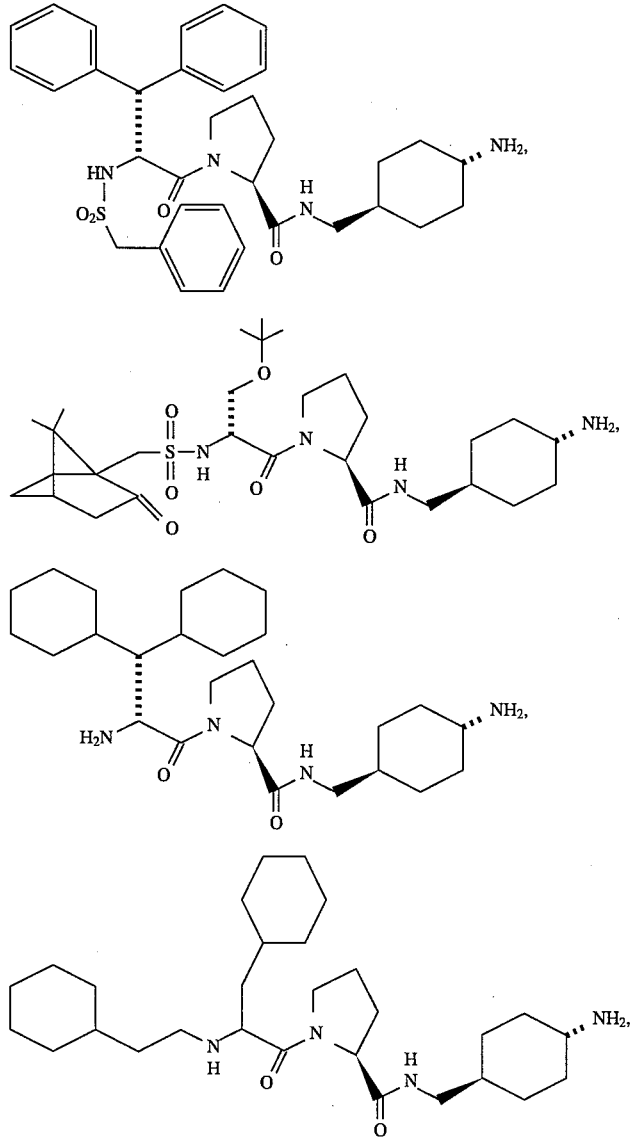

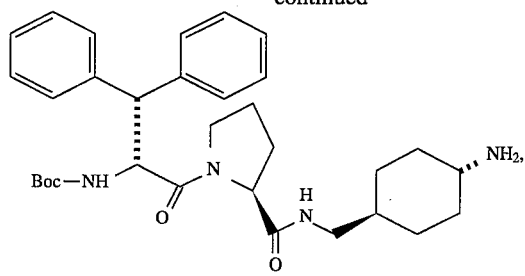
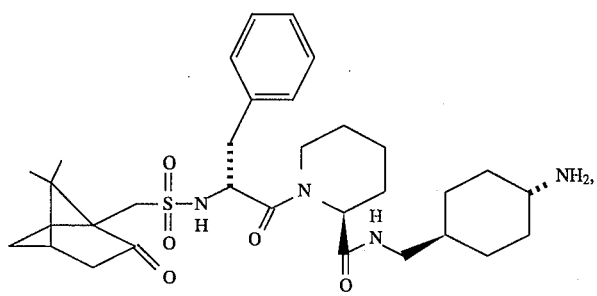
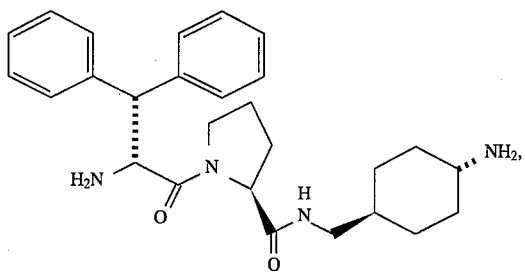
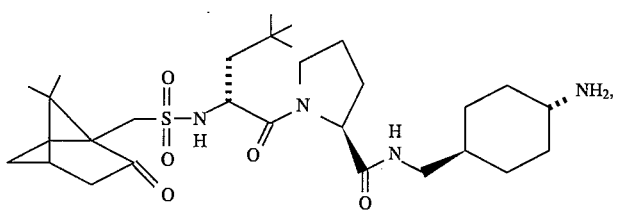
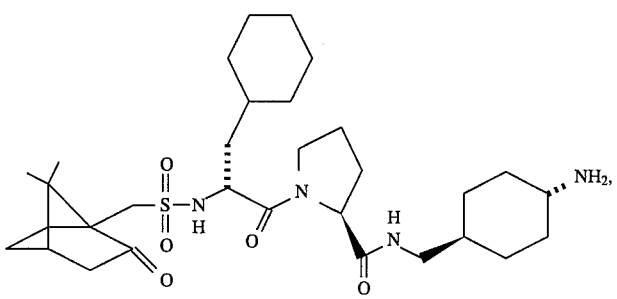
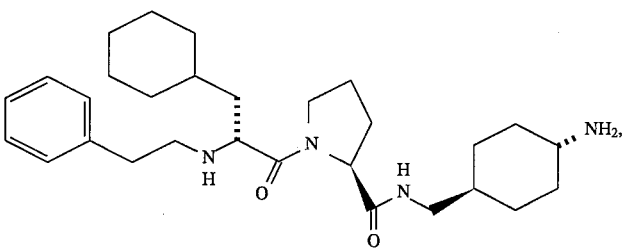

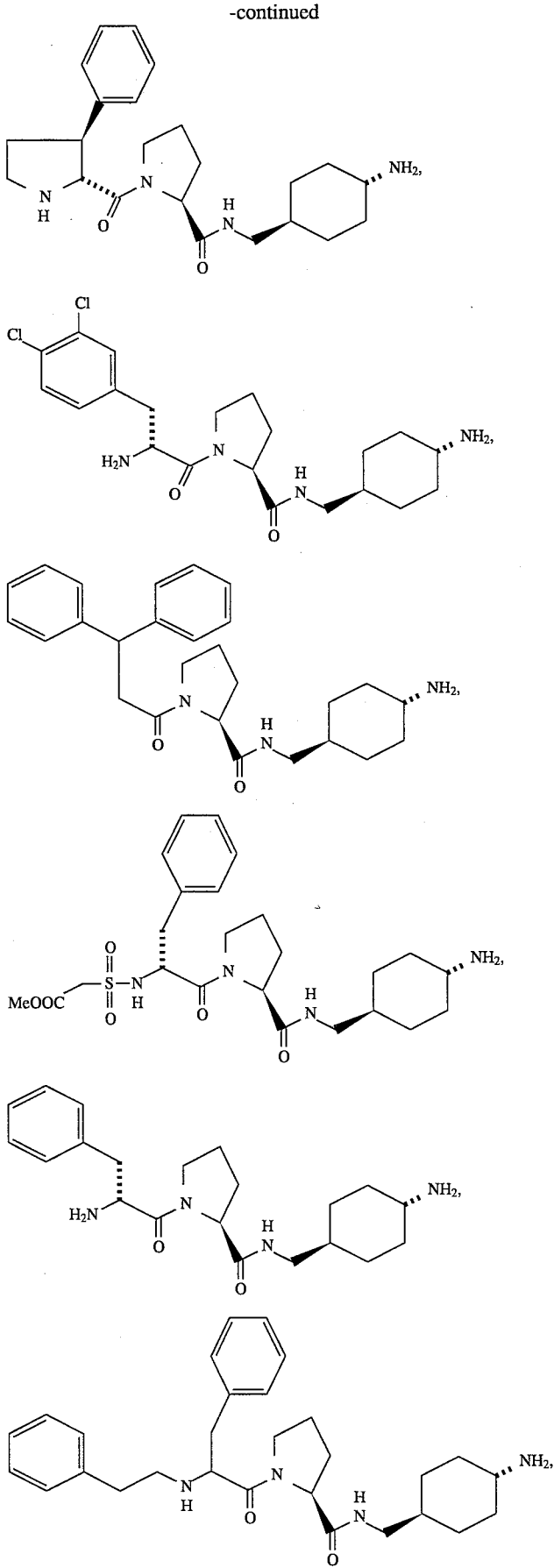

-continued
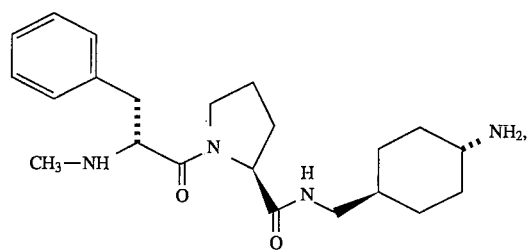
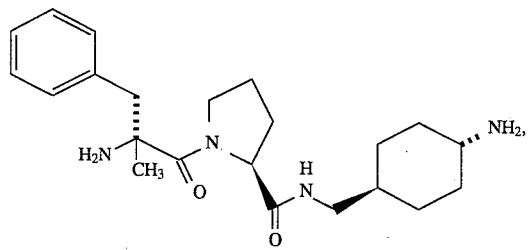
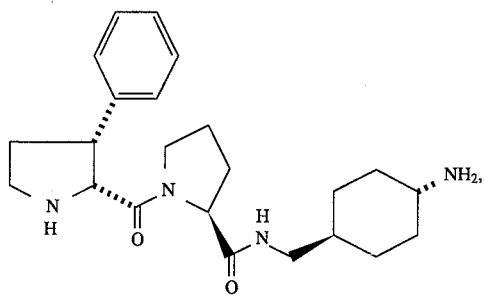
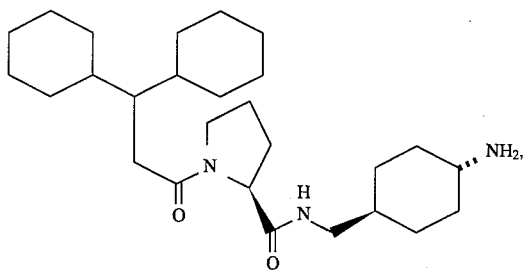
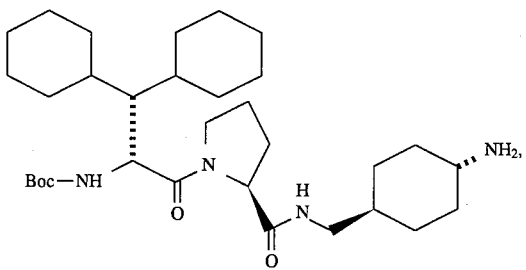
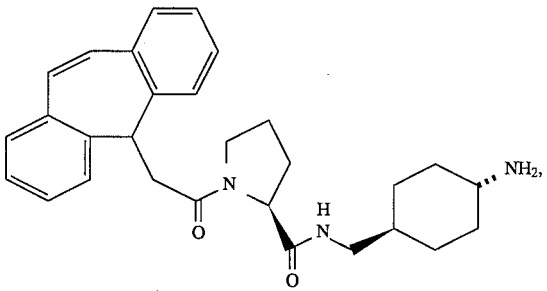

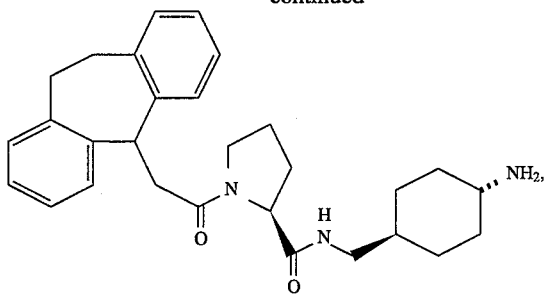

and

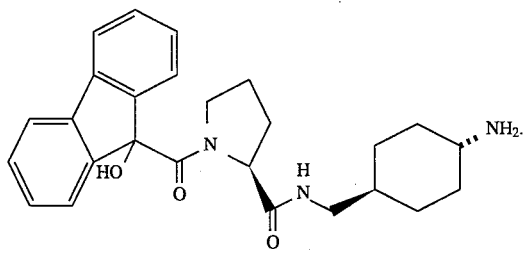

In another class of compounds of the invention, X is NR$^1$CH$_2$; R$^1$ is hydrogen or C$_{1-4}$ alkyl; Y is (CH$_2$)$_r$; and r is 2. Specific emboments of this class include

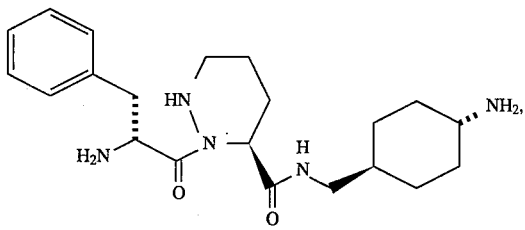

and

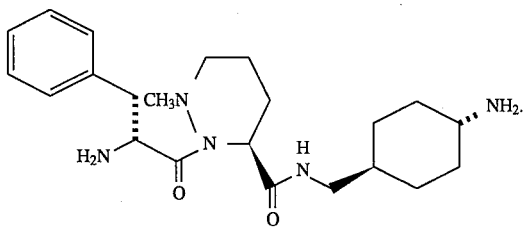

The compounds of the present invention, may have asymmetric centers and occur as racemates, racemic mixtures and as individual diastereomers, or enantiomers with all isomeric forms being included in the present invention. A racemate or racemic mixture does not imply a 50:50 mixture of stereoisomers.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

The term heterocycle or heterocyclic, as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quatemized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quatemized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Amide couplings used to form the compounds of this invention are typically performed by the carbodiimide method with reagents such as dicyclohexylcarbodiimide, or 1-ethyl-3-(3-dimethyl-aminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

The compounds shown in the tables below are exemplary compounds of the present invention:

TABLE 1

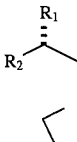

| $R_1$ | $R_2$ | Ki vs Thrombin (nM) |
|---|---|---|
| PhCH$_2$ | H | 680 |
| C$_6$H$_{11}$CH$_2$ | H | 150 |
| 3,4-Cl$_2$—PhCH$_2$ | NH$_2$ | 1.5 |
| PhCH$_2$ | NH$_2$ | 3.4 |
| |  | 47 |
| 3,4-Cl$_2$—PhCH$_2$ | CH$_3$NH | 2.9 |
| | 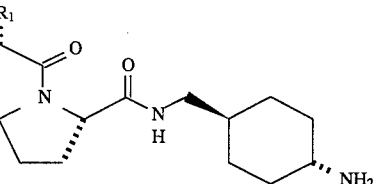 | 152 |
| PhCH$_2$ | CH$_3$SO$_2$NH | 17 |
| 3,4-Cl$_2$—PhCH$_2$ | H | 414 |

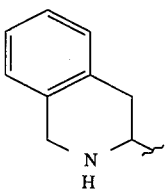

| $R_2$ | $R_1$ | Ki (nM) vs thrombin |
|---|---|---|
| H | H | >10000 |
| CH$_3$NH | 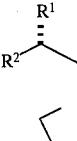 | 2.3 |

TABLE 1-continued

| Group 1 | Group 2 | Value |
|---|---|---|
| NH₂ | 2-naphthylmethyl (CH₂-naphthalene) | 27 |
| NH₂ | 3-pyridylmethyl (CH₂-pyridine) | 30 |
| OH | benzyl (CH₂-phenyl) | 63 |
| AcNH | benzyl (CH₂-phenyl) | 170 |
| BocNH | benzyl (CH₂-phenyl) | 9.4 |
| CbzNH | benzyl (CH₂-phenyl) | 3.7 |
| 4-pyridyl-CH₂OCONH | benzyl (CH₂-phenyl) | 15 |
| BocNH | phenyl (direct attachment) | 6.8 |
| BocNH | cyclohexylmethyl (CH₂-cyclohexyl) | 12 |
| BocNH | 2-phenylethyl (CH₂CH₂-phenyl) | 50 |
| BocNH | CH₂O—tBu | 6 |
| CbzNH | CH₂—tBu | 2.3 |
| CbzNH | 3-indolylmethyl (CH₂-indole) | 16 |
| Boc—NH | α-(tert-butoxy)benzyl | 8.0 |
| CF₃CH₂SO₂NH | cyclohexylethyl | 3.0 |

TABLE 1-continued

| G | Ki (nM vs thrombin) |
|---|---|
| PhCH$_2$CH$_2$NH—[benzyl group] | 4.0 |
| Boc—NH—[CH(OtBu)(Ph)] | 200 |

TABLE 2

[Structure: G-C(=O)-N-pyrrolidine-C(=O)-NH-CH$_2$-cyclohexyl-NH$_2$]

| G | Ki (nM vs thrombin) |
|---|---|
| Ph$_2$CH-CH(NH$_2$)- | 0.12 |
| Ph$_2$CH-CH$_2$-CH$_2$- | 2.0 |
| PhCH$_2$-SO$_2$-NH-CH(CH$_2$Ph)- | 0.4 |
| Ph$_2$CH-CH(NHSO$_2$CH$_2$Ph)- | 0.0025 |
| PhCH$_2$-SO$_2$-NH-CH(iPr)- | 0.4 |
| HO$_2$C-CH$_2$-NH-CH(CH$_2$Ph)- | 1.3 |
| Ph$_2$CH-CH(NHBoc)- | 0.102 |
| camphorsulfonyl-NH-CH(CH$_2$O-t-Bu)- | 0.05 |

TABLE 2-continued

| G | Ki (nM) |
|---|---|
| (pyrrolidine carbonyl, G-attached) | |
| (camphorsulfonamide group) | 0.1 |

| G | Ki (nM) |
|---|---|
| (9-hydroxyfluorenyl) | 1.5 |
| (benzodioxane-like) | 55 |
| (dibenzothiophene hydroxyl) | 3 |

The following synthetic routes can be used to prepare compounds of the invention. Using method I (as exemplified by example 1), trans-4-t-butoxycarbonylamino-cyclohexyl-methaneamine (1-3) is coupled to a protected dipeptide such as N-methyl-D-phenylalanyl-L-proline using standard amide coupling procedures. The BOC protecting groups can then be removed using a strong acid such as HCl gas.

METHOD 1

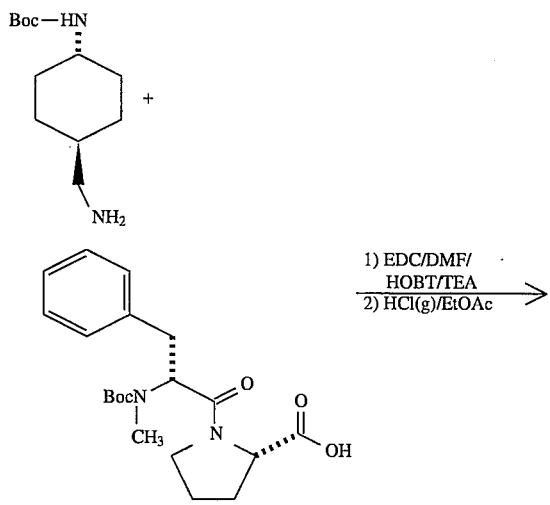

A second method for constructing the compounds of general structure I (as exemplified by example 18) is to react trans-4-benzyloxycarbonylamino-cyclohexyl-methaneamine with a protected amino acid such as Boc-L-proline. The Amino acid group is removed and the freed amine is then coupled with the suitable carboxylic acid. The CBZ group is then removed using reducing conditions.

METHOD 2

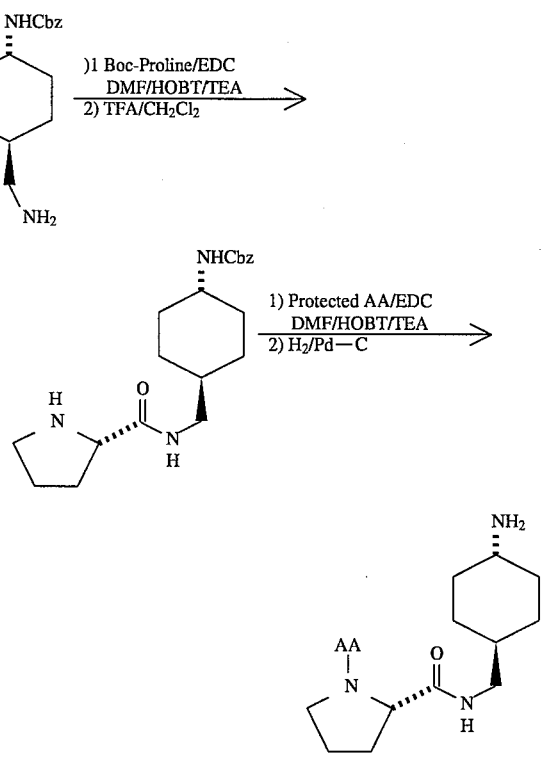

A third preferred method (as exemplified by example 5) is to couple the protected Boc-amino-cyclohexylmethanamine-L-proline with the desired acid followed by removal of the Boc protecting group to give the requisite compound.

METHOD 3
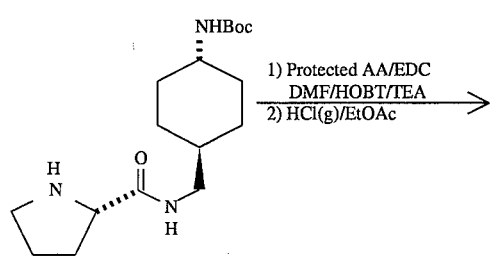
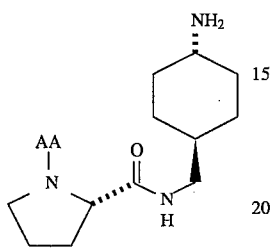
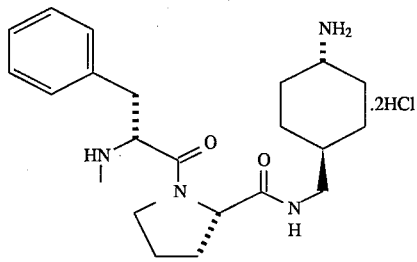
For example, this method can be used to prepare as shown in Example 1.
EXAMPLE 1
Preparation of trans-4-Aminocyclohexylmethyl N-Methyl-D-phenylalanyl-L-proline amide
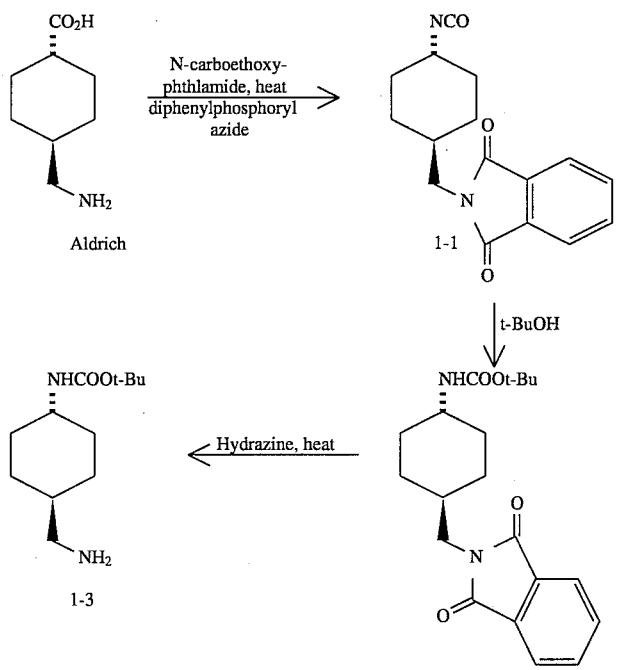

-continued

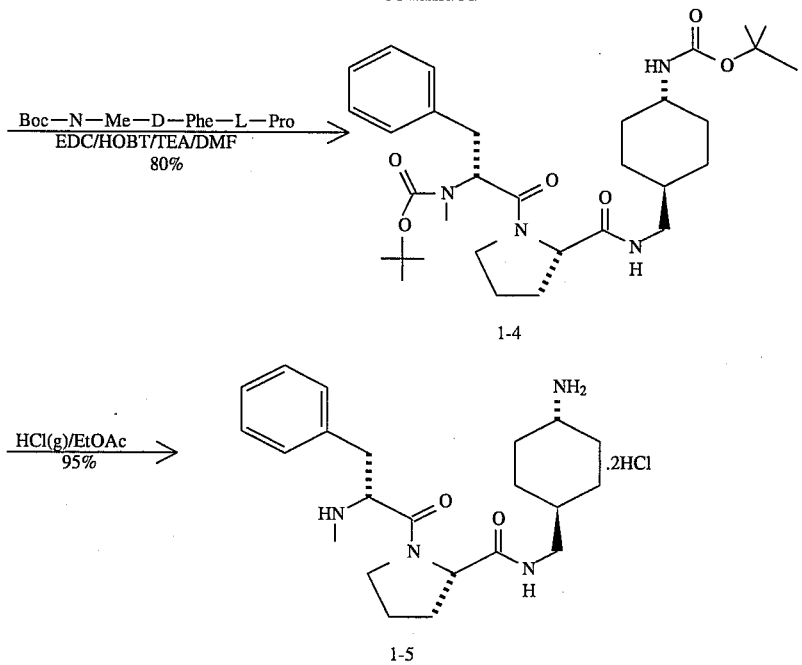

Step 1

Preparation of N-(trans-4-Carboxycyclohexylmethyl)phthalimide

N-carboethoxyphthalimide (21.9 g, 0.10 mol), trans-4-(aminomethyl)cyclohexane carboxylic acid (15.7 g, 0.10 mol) and triethylamine (14 mL) were stirred in 100 mL THF and the mixture refluxed 18 h. The nearly clear solution was poured into 400 ml water containing 10 mL glac. HOAc with rapid stirring and the precipitated product collected by suction and dried in a vacuum oven at 80° C., mp 190°–192°.

Step 2

Preparation of N-(trans-4-Isocyanatocyclohexylmethyl)phthalimide

The product from example 1, step 1 was stirred in 200 ml $CCl_4$ containing 10 mL $SOCl_2$ and the mixture refluxed under a drying tube until the solution remained clear on cooling and gas evolution ceased. The mixture was concentrated in vacuo to 100 ml and treated with 14.0 mL trimethylsilyl azide at reflux for 18 h. The resulting solution was concentrated to give the crude title isocyanate.

Step 3

Preparation of N-(4-tertbutoxycarbonylamino)cyclohexylmethyl phthalimide

The crude product from example 1, step 2 was treated with a solution of lithium tert butoxide in THF for 2 hours at room temperature to give a dark solution which was diluted with aqueous acetic acid and ice to precipitate the crude product which is recrystallized from 1-chlorobutane to give beige needles of the title urethane, mp. 163°–165°.

The above urethane phthalimide was treated with 1 equiv anhydrous hydrazine in isopropanol for 18 h at room temperature followed by 4 h reflux. The mixture was concentrated, diluted with cold aqueous acetic acid and filtered to remove phthalazinedione. The aqueous layer was basified with NaOH followed by extraction with ethyl acetate, drying, and evaporation to afford the desired product 1-3 as a solid.

Step 4

Preparation of trans-4-Aminocyclohexylmethyl N-Methyl-D-phenylalanyl-L-proline amide 1-3 (37 mg, 0.16 mmol), Boc-N-Me-D-phenylalanyl-L-proline (60 mg, 0.159 mmol), EDC (31 mg, 0.16 mmol), $HOBT.H_2O$ (22 mg, 0.16 mmol), and triethyl amine (TEA, 0.045 ml, 0.32 mmol) were dissolved in 0.5 ml DMF, adding TEA last. 1.5 ml DMF was added to facilitate stirring. The mixture was stirred under argon overnight.

After overnight stirring, the solution was rotovaped to dryness, partitioned between $CHCl_3$ and 1M citric acid, washed with 10% $Na_2CO_2$, dried over $MgSO_4$ and solvents removed to give 92 mg of a colorless oil.

The oil was dissolved in 3 ml $CH_2Cl_2$, 1.5 ml TFA was added, and the mixture stirred under argon for 1 h. The stirred solution was rotovaped to dryness, dissolved in $CHCl_3$, washed with 10% $Na_2CO_3$, and dried over $MgSO_4$. Solvents were removed to give 35 mg of an oil.

The oil was chromatographed on 5 g fine $SiO_2$ using 80:20:2 C—M—$NH_4OH$. Pure fractions were combined to give 30 mg of colorless glass.

Glass was suspended in 4 ml $Et_2O$. 17 mL of 9.9M Ethanolic HCl was added and stirred at room temperature. Filtered off gummy solid, dried at 65° C. at high vacuum overnight to give 18 mg of 1-5.

EXAMPLE 2

Preparation of N-trans-4-Aminocyclohexylmethyl Hydrocinnamyl-L-proline amide

Step 1

Hydrocinnamyl-L-Proline

Hydrocinnamic acid (1.63 g., 11 mmol) and L-proline-OMe HCl (2.19 g., 13.2 mmol) were dissolved in 110 ml. of dimethylacetamide (DMAc), followed by the addition of 2.19 g. (14.3 mmol) of HOBt and adjustment to pH 8 with N-methylmorpholine (NMM). Then EDC (3.16 g., 16.5 mmol) was added and the solution stirred for 20 hr., followed by concentration in vacuo and extractive workup with EtOAc to afford 2.97 g. of oily residue, which was purified by chromatography on silica gel to yield 2.68 g. of methyl ester. This intermediate was saponified in 100 ml. of 50:50 THF/$H_2O$ using 5.2 ml. of 2.17 N LiOH for 3 hr., to give, after acidification with dil. KHSO4, removal of the volatile solvents in vacuo, and extractive workup with EtOAc, the title compound as a colorless oil.

Step 2 trans-4-Aminocyclohexylmethyl Hydrocinnamyl-L-proline amide

Hydrocinnamyl-L-Proline (238 mg., 0.96 mmol) and N-(trans-4-tert-butoxycarbonyl)-aminocyclohexylmethylamine (200 mg., 0.88 mmol) were dissolved in 20 ml. of DMF, followed by addition of 161 mg.( 1.06 mmol) of HOBt and adjustment to pH 8 with NMM. Then is EDC (219 mg., 1.14 mmol) was added and the solution stirred for 2 days, followed by concentration in vacuo and extractive workup with EtOAc to afford a tacky solid. This material was dissolved in 5 ml. of 100% TFA, let 15 min., and the TFA was removed under reduced pressure and the product purified by preparative HPLC using a TFA(0.1%)-$CH_3CN$ gradient. Lyophilization of pure fractions gave the title compound as a trifluoroacetic acid hydrate salt: $C_{21}H_{31}N_3O_2 \cdot CF_3COOH \cdot H_2O$ (FAB MS 358 (M+H$^+$)).

EXAMPLE 3

Preparation of trans-4-Aminocyclohexylmethyl 3-Cyclohexylpropionyl-L-proline amide A solution of trans-4-Aminocyclohexylmethyl hydrocinnamyl-L-proline amide in 50 ml. of 50% HOAc was shaken in a Parr apparatus with 80 mg. of $PtO_2$ for 20 hr. The solution was decanted and concentrated in vacuo, and the residue was dissolved in water and the product purified by preparative HPLC using a TFA(0.1%)-$CH_3CN$ gradient. Lyophilization of pure fractions gave the title compound as a trifluoroacetic acid hydrate salt: $C_{24}H_{34}N_4O_4 \cdot CF_3COOH \cdot H_2O$ (FAB MS 443 (M+H$^+$)).

EXAMPLE 4

Preparation of trans-4-Aminocyclohexylmethyl D-phenylalanyl-L-proline-amide

Boc-D-phenylalanyl-L-proline-OH (293 mg., 0.809 mmol) and N-(trans-4-tert-butoxycarbonyl)-aminocyclohexylmethylamine (151 mg., 0.66 mmol) were dissolved in 15 ml. of DMa, followed by addition of 134 mg. (0.876 mmol) of HOBt and adjustment to pH 7 with NMM. Then EDC (167 mg., 0.870 mmol) was added and the solution stirred for 2 days, followed by concentration in vacuo and extractive workup with EtOAc to afford 385 mg. of a tacky solid. This material was dissolved in 10 ml. of 100% TFA, let 20 min., and the TFA was removed under reduced pressure and the product purified by preparative HPLC using a TFA(0.1%)-$CH_3CN$ gradient. Lyophilization of pure fractions gave the title compound as a trifluoroacetic acid hydrate salt: $C_{21}H_{32}N_4O_2 \cdot CF_3COOH \cdot H_2O$ (FAB MS 373 (M+H$^+$)).

EXAMPLE 5

Preparation of trans-4-Aminocyclohexylmethyl 1,4-Benzodioxane-2-carboxyl-L-proline amide 1,4-Benzodioxane-2-carboxylic acid (61 mg., 0.337 mmol) and trans-4-(tert-butoxycarbonyl-amino)cyclohexylmethyl L-proline amide (87 mg., 0.266 mmol) were dissolved in 15 ml. of DMAc, followed by addition of 51 mg. (0.330 mmol) of HOBt and adjustment to pH 8 with NMM. Then EDC (63 mg., 0.328 mmol) was added and the solution stirred for 2 days, followed by concentration in vacuo and extractive workup with EtOAc to afford 126 mg. of a tacky solid. This material was dissolved in 10 ml. of 1:1 TFA-$CH_2Cl_2$, let 20 min., and the TFA was removed under reduced pressure and the product purified by preparative HPLC using a TFA(0.1%)-$CH_3CN$ gradient. Lyophilization of pure fractions gave the title compound as a trifluoroacetic acid hydrate salt: $C_{21}H_{29}N_3O_4 \cdot CF_3COOH \cdot H_2O$ (FAB MS 388 (M+H$^+$)).

EXAMPLE 6

Preparation of trans-4-Aminocyclohexylmethyl N-Me-D-phenylalanyl-L-azetidine-2-carboxy amide Step 1

Preparation of trans-4-Aminocyclohexylmethyl (H) L-Azetidine-2-carboxy amide

Boc-L-azetidine-2-carboxylic acid (91 mg., 0.450 mmol) and N-(trans-4-benzyloxycarbonyl-aminocyclohexylmethylamine (89 mg., 0.340 mmol) were dissolved in 15 ml. of DMAc, followed by addition of 77 mg. (0.503 mmol) of HOBt and adjustment to pH 8 with NMM. Then EDC (83 mg., 0.432 mmol) was added and the solution stirred for 2 days, followed by concentration in vacuo and extractive workup with EtOAc to afford 140 mg. of a tacky solid. This material was dispersed in 10 ml. of EtOAc, the internal temperature was lowered to −40 deg, and the solution was saturated with HCl (warmed to −10 deg). After 5 min. the mixture was purged with $N_2$ for 1 hr., and the solvent was removed at reduced pressure to give 115 mg. of the title compound as its HCl salt.

Step 2

Preparation of trans-4-Aminocyclohexylmethyl N-Me-D-phenylalanyl-L-azetidine-2-carboxy amide Boc-N-Me-D-phenylalanyl-OH (119 mg., 0.427 mmol) and (H) L-azetidine-2-carboxy-(N-trans-4-aminocyclohexylmethyl) amide HCl salt (116 mg., 0.334 mmol) were dissolved in 15 ml. of DMAc, followed by addition of 62 mg. (0.405 mmol) of HOBt and adjustment to pH 8 with NMM. Then EDC (93 mg., 0.484 mmol) was added and the solution stirred for 20 hr., followed by concentration in vacuo and extractive workup with EtOAc to afford 179 mg. of a tacky solid. This sample was placed in a Kel-F vessel charged with 0.5 ml. of anisole and 10 ml. of HF, stirred at 0 deg for 1 hr., and the HF was removed under reduced pressure. The crude product was precipitated by the addition of 1:1 ether-petroleum ether, collected by filtration, and purified by preparative HPLC using a TFA(0.1%)-$CH_3CN$ gradient. Lyophilization of pure fractions gave the title compound as a trifluoroacetic acid hydrate salt: $C_{21}H_{32}N_4O_2 \cdot CF_3COOH \cdot H_2O$ (FAB MS 373 (M+H$^+$)).

EXAMPLE 7

Preparation of trans-4-Aminocyclohexylmethyl L- and D-(3,3)-diphenylalanyl-L-proline amide.

To an ice cooled solution of 250 mg (0.73 mmol) of Boc-D,L-(3,3)-diphenylalanine, 0.204 ml (1.46 mmol) of triethylamine, and 238 mg (0.73 mmol) of trans-4-(t butoxycarbonylamino)cyclohexylmethyl proline amide in 2 ml of methylene chloride was added 186 mg (0.73 mmol) of BOP-chloride. The solution was stirred at 0° C. for 30 min., then at room temp. for 18 hrs. The reaction was diluted with 3× its' volume of EtOAc and 0.5× its' volume of aq. 10% citric acid solution. The organic layer was washed with water and brine, and was dried (anh. $MgSO_4$). Filtration and concentration gave a white foam. The crude foam was purified via column chromatography over silica gel with 5% MeOH/$CHCl_3$ to give 400 mg(85%) of the coupling product as a white foam. The foam was dissolved in 2 ml $CH_2Cl_2$/2 ml trifluoroactic acid under a nitrogen atmosphere, and the solution stirred at room temp. for 18 hrs. The reaction was concentrated in vacuo to provide a tan foam consisting of a mixture of product diastereomers at the diphenylalanine alpha carbon. The mixture was separated via reverse phase ($C_{18}$) preparatory HPLC to provide the two pure diastereomers. The more polar diastereomer was isolated as a clear glass. The glass was suspended in $Et_2O$ containing a few drops of EtOAc, and the glass scratched, sonicated, and filtered to give 65 mg of a glassy white solid. Anal. ($C_{27}H_{26}N_4O_2$.2.35 TFA. 0.70 $H_2O$),CHN. High Res. FABMS: M+1 theo.=449.29165, obs.=449.29110. The less polar diastereomer was crystallized in a similar fashion to give 80 mg of a glassy white solid. Anal. ($C_{27}H_{26}N_4O_2$. 2.30TFA.0.70 $H_2O$), CHN. High Res. FABMS: M+1 theo.= 449.29165, obs.=449.29128. The less polar diastereomer was the more active isomer in a thrombin inhibition assay, and X-ray crystallography of the thrombin bound complex with this compound indicated that the stereochemistry at the diphenylalanine alpha carbon was (R).

EXAMPLE 8

Preparation of trans-4-Amino-cyclohexylmethyl N-(3,3-diphenyl-1-oxo-propan-1-yl)-L-proline amide.

To a stirred solution of 100 mg (0.31 mmol) of trans-4-(t-Butoxycarbonyl)aminocyclohexylmethyl L-proline amide, 70 mg (0.31 mmol) of 3,3 diphenylpropionic acid, 46 mg (0.34 mmol) of HOBT, and 34 mg (0.34 mmol) of triethylamine in 2 ml of anh. DMF under a nitrogen atmosphere was added 65 mg (0.34 mmol) of EDC. The resulting solution was stirred at room temp. for 18 h. The reaction was diluted with 2× its' volume of aq. 10% citric acid solution, and the mixture extracted 2× with EtOAc. The combined EtOAc extracts were washed with water and brine, and were dried over anh. $MgSO_4$. Filtration and concentration gave crude product as a yellow oil. The product was purified via column chromatography over silica gel with 3:2 EtOAc/$CHCL_3$ to give 109 mg (64%) of product as a clear glass.

The product was immediately dissolved in 2 ml $CH_2Cl_2$/2 ml trifluoroacetic acid, and the solution stirred at room temp. under a nitrogen atmosphere for 18 h. The reaction was concentrated in vacuo to give a tan foam. The crude product was purified via reverse phase prep HPLC to provide pure product as a clear glass. The glass was suspended in $Et_2O$ containing a few drops of hexanes, and scratching and filtration provided 65 mg of the desired product as a white solid, MP=120°–123° C. Anal. ($C_{27}H_{35}N_3O_2$.1.60TFA.0.45$H_2O$), CHN. High Res. FABMS: M+1 theo.=434.28075, obs.=434.28204.

EXAMPLE 9

Preparation of trans-4-Amino-cyclohexylmethyl N-(benzylsulfony)-D and L-3,3-diphenylalanyl-L-proline amide Step 1

Preparation of D,L-3,3-diphenylalanine methyl ester hydrochloride.

To a stirred solution of 600 mg( 1.76 mmol) of Boc-D, L-3,3-diphenylalanine in 7 ml of anh. DMF under a nitrogen atmosphere was added 195 mg (2.32 mmol) of $NaHCO_3$, followed by 942 mg (6.64 mmol) of $CH_3I$. The resulting mixture was stirred at room temperature for 18 h. The reaction was diluted with aq. 10% citric acid solution, and the resulting suspension extracted 2× with EtOAc. The combined extracts were washed with water and brine, and were dried over anh. $MgSO_4$. Filtration and concentration provided a yellow oil. The oil was dissolved in 2 ml of EtOAc, and the solution cooled to 0° C. and bubbled with HCL gas for 5 min. The resulting solution was capped and stirred a 0° C. for 15 min. The cold solution was scratched, and a white crystalline solid precicptated out. The solid was collected via filtration, washed with $Et_{2O}$, and dried in vacuo to give 376 mg (73%) of desired product, MP=221°–222° C. (dec.). High Res. FABMS: M+1 theo.=256.13375, obs.= 256.13287.

Step 2

Preparation of N-(benzylsulfonyl)-D,L-3,3-diphenylalanine-methyl ester.

To an ice water cooled solution of 5.80 g (19.88 mmol) of D,L-3,3-diphenylalanine methyl ester hydrochloride and 3.79 g (19.88 mmol) of benzylsulfonyl chloride in 50 ml pyridine in a nitrogen atmosphere was added 2.43 g (19.88 mmol) of 4-dimethylaminopyridine. The suspension was stirred in the bath for 5 min., then at room temp. for 18 h. An additional 0.30 eq. of each reagent was added, and stirring continued for an additional 4 h. The reaction was concentrated in vacuo, and the residue partitioned between aq. 10% citric acid solution and EtOAc. The aqueous layer was reextracted with EtOAc, and the combined extracts washed with water and brine. Drying and concentration in vacuo provided 6 g of crude product as a tacky yellow solid. Column chromatography over silica gel with 14:1 $CHCl_3$/EtOAc provided 4.85 g(60%) of desired product as a white cryst. solid, MP=162°–163° C. High Res. FAB MS: M+theo.=410.14260, obs.=410.14303.

Step 3

Preparation of trans-4-Amino-cyclohexylmethyl N-(benzylsulfonyl)-D and L-3,3-diphenylalanyl-L-proline amide.

A solution of 215 mg (0.53 mmol) of N-(benzylsulfonyl)-D,L-3,3-diphenylalanine-methyl ester in 3 ml aq. 2N LiOH/3 ml DME was stirred at room temperature for 48 h. The reaction was conc. to remove DME, and was acidified with aq. 10% citric acid solution. The aqueous soln. was extracted 2× with EtOAc. The combined extracts were washed with water and brine and were dried (anh. $MgSO_4$). Filtration and concentration provided 200 mg (95%) of the free proline acid. A stirred solution of the 200 mg (0.51 mmol) sample of acid, 166 mg (0.51 mmol) of trans-4-(t-butoxycarbonyl)amino-cyclohexylmethyl L-proline amide, and 184 mg (0.51 mmol) of chloro-N,N,N',N'-bis(pentamethylene) formamidinium hexafluorophosphate (Fluka) in 2 ml $CH_2Cl_2$ cooled to 0° C. in a nitrogen atmosphere was treated with 132 mg (1.02 mmol) of diisopropylethylamine. The solution was stirred at 0° C. for 5 min., and was stirred at room temp. for 2 h. The solution was concentrated in vacuo, and the residue partitioned between aq. 10% citric acid and EtOAc. The aqueous layer was reextracted 2× with EtOAc, and the combined extracts washed with 5% aq. $NaHCO_3$ soln., water, and brine. Drying (anh. $MgSO_4$) and concentration in vacuo provided crude product as a tan foam. The foam was purified via column chromatography over silica gel with 5% MeOH/CHCl$_3$ to give 161 mg (44% based on acid) of the coupling product. The product was dissolved in 1.5 ml CH$_2$Cl$_2$/1.5 ml trifluoroacetic acid, and the solution stirred at room temp. in a nitrogen atmosphere for 2 h. The reaction was concentrated in vacuo to provide a yellow oil, which consisted of a mixture of diastereomers at the diphenylalanine alpha carbon. The mixture was separated via reverse phase (C$_{18}$) preparatory HPLC to provide pure samples of each diastereomer. The earlier eluting diastereomer was isolated after lyophilization as a clear glass. The glass was suspended in ether, scratched and filtered to give 30 mg of pure more polar diastereomer as a white glassy solid. Anal. (C$_{34}$H$_{42}$N$_4$O$_4$S.1.35 TFA.2.00H$_2$O), CHN. FAB MS: M+1=603. The less polar diastereomer was isolated after lyophilization as a white glassy powder. Anal. (C$_{34}$H$_{42}$N$_4$O$_4$S.1.45TFA.0.70H$_2$O), CHN. High Res. FAB MS: M+1 theo.=603.30050, obs.= 603.29885. The less polar diastereomer was tentatively assigned the (R) stereochemistry (corresponds to the (D) amino acid) at the diphenylalanine alpha carbon, as it was determined to be the more active isomer in a thrombin inhibition assay.

EXAMPLE 10

Preparation of trans-4-Aminocyclohexylmethyl N-(2-naphthylsulfonyl)-glycl-L-proline amide To a stirred solution of 82 mg (0.34 mmol) of N-(2-naphthylsulfonyl)glycine, 100 mg (0.31 mmol) of trans-4-(t-butoxycarbonyl)aminocyclohexylmethyl L-proline-amide, 46 mg (0.34 mmol) HOBT, and 34 mg (0.34 mmol) of triethylamine in 2 ml anh. DMF under a nitrogen atmosphere was added 65 mg (0.34 mmol) of EDC, and the solution stirred at room temperature for 18 h. The reaction was diluted with 2× its volume of aq. 10% citric acid solution, and was extracted 2× with EtOAc. The combined EtOAc extracts were washed with water and brine, and dried over anh. MgSO$_4$. Concentration provided approx. 200 mg of a white foam. The crude product was purified via column chromatography over silica gel with 4% MeOH/CHCl$_3$ to give 90 mg of purified coupling product as a clear glass. The glass was dissolved in 2 ml EtOAc/0.5 ml CHCl$_3$, and the solution cooled to 0° C. The solution was bubbled with HCl gas for 5 min. at 0° C., and was stirred in the cold for an additional 20 min. Scratching the side of the flask with a glass rod induced crystallization, and the precipitated product was filtered off and washed with EtOAc and Et$_2$O. Drying provided 50 mg of product as a white solid, MP=189°–191° C. Anal.(C$_{24}$H$_{32}$N$_4$O$_4$S.HCl.0.20CHCl$_3$.0.20H$_2$O), CHN. FAB MS: M=1=473.

EXAMPLE 11

Preparation of trans-4-Aminocyclohexylmethyl N-(benzylsulfonyl)-D-phenylalanyl-L-proline amide Step 1

Preparation of N-benzenesulfonyl-L-phenylalanine (D)-PheOH (0.83 g 5.0 mmol) was dissolved in 40 mL dioxane by addition of 5 ml 1N NaOH. The resulting solution was treated dropwise with phenylmethanesulfonyl chloride with rapid stirring at room temperature. After 1 hour, the mixture was diluted with 10 mL H$_2$O and filtered. The filtrate was treated with 2.5 mL aq. KHSO$_4$ and concentrated in vacuo. Extraction of the residue with CHCl$_3$ and concentration of the CHCl$_3$ gave the title compound which melted at 150°–152° C. (n-butylchloride).

Step 2

Preparation of trans-4-Aminocyclohexylmethyl N-phenylmethanesulfonyl-D-phenylalanyl-L-proline amide N-phenylmethanesulfonyl-D-phenylalanine ( 108 mg, 0.33 mmol) and N-(trans-4-tert. butyloxycarbonylaminocyclohexylmethyl L-proline amide (130 mg) were coupled with hydroxybenztriazole hydrate (55 mg) and EDC-HCl (70 mg) in 1 mL DMF containing triethylamine (100 ml). The mixture was stirred under N$_2$ at room temperature overnight, then diluted with 10 mL of 10% aqueous citric acid and extracted with CH$_2$C$_{12.}$ The CH$_2$Cl$_2$ extracts were washed with aqueous Na$_2$CO$_3$, dried (Na$_2$SO$_4$), filtered and concentrated in vacuo to give the crude Boc derivative of the title compound. Chromatography on silica gel afforded the pure Boc derivative (130 mg) which was treated with 0.3 mL trifluoroacetic acid in 1 mL CH$_2$Cl$_2$ for 6 hours at room temperature. The mixture was concentrated and the residue purified by preparative HPLC using a trifluroacetic acid (0.1%)-CH$_3$CN gradient. Lyophilization of pure fractions gave the title compound as a trifluoroacetic acid hydrate salt: C$_{28}$H$_{38}$N$_4$O$_4$S.CF$_3$CO$_2$H.H$_2$O (FAB MS 527.1 (M+H$^+$)) L-372,130.

EXAMPLE 12

Preparation of trans-4-aminocyclohexylmethyl N-methanesulfonyl-D-phenylalanyl-L-proline amide Step 1

Preparation of N-methanesulfonyl-D-phenylalanyl

H-D-phenylalanyl-benzylester (toluenesulfonate salt, 2.14 g, 5.0 mmol) and triethylamine (1.4 mL) were dissolved in 25 mL CH$_2$Cl$_2$ and the solution treated with methanesulfonyl chloride (0.39 mL, 5.0 mmol). After 30 minutes at room temperature, the solution was washed with 1.2N HCl, water, and dried (Na$_2$SO$_4$). Concentration of the filtered CH$_2$Cl$_2$ gave 2.3 g of the benzyl ester. The crude product was crystallized from n-butyl chloride to give a white solid, mp 76°–77°.

The crystalline ester was hydrogenolyzed in 50 mL abs. EtOH with 100 mg 10% Pd-C and balloon pressure of H$_2$. After 18 hours at room temperature, the mixture was filtered through celite and the filtrate concentrated. The crude title acid was crystallized by trituration with n-butyl chloride, mp 103°–105°.

Step 2

Preparation of trans-4-Aminocyclohexylmethyl N-methanesulfonyl-D-phenylalanyl-L-proline amide The acid of Example 13, step 1 was coupled with N-(trans-4-tert. butyloxycarbonlaminocyclohexylmethyl) L-proline amide using standard conditions. The crude Boc protected intermediate was deblocked with CF$_3$CO$_2$H in CH$_2$Cl$_2$ and the crude product crystallized by trituration with ether to give the title compound C,H,N for C$_{22}$H$_{34}$N$_4$O$_4$S.CF$_3$CO$_2$H.H$_2$O).

EXAMPLE 13

Preparation of trans-4-Aminocyclohexylmethyl trans-threo-5-phenyl-oxazolidine-4-carbonyl-L-proline amide dl-trans-threo-5-Phenyl-oxazolidine-4-carboxylic acid (21 mg, 1.05 mmol) was coupled with trans-4-(tert. butoxycarbonyl)aminocyclohexylmethyl L-proline amide (330 mg, 1.0 mmol) using hydroxybenztriazole hydrate (150 mg) and EDC. HCl (200 mg) with triethylamine in DMF as in previous examples. The crude reaction product from $CH_2CL_2$ extraction was crystallized from EtOAc to give a solid fraction rich in one diastereomer (140 mg). This solid was deblocked with TFA in $CH_2Cl_2$ and the crude product purified by preparative HPLC ($CF_3CO_2H—H_2O:CH_3CN$) to give diastereomer A of the title compound after trituration with EtOAc-Et$_2$O (CN, CH for $C_{22}H_{30}N_4O_6.CF3CO2H.1.65\ H2O$); HPLC 99% pure A, 4-(R).

The EtOAc soluble portion of the coupling product was deblocked with $CF_3CO_2H$ in $CH_2Cl_2$ and the diastereomer B purified by preparative HPLC ($CF_3CO_2H—H_2O:CH_3CN$) (N, C, H for $C_{22}H_{30}N_4O_2.CF_3CO_2H.165H_2O$, FAB MS 415 $(M+H^+)$); 4-(S).

EXAMPLE 14

Preparation of trans-4-(benzyloxycarbonyl)aminocyclohexylmethyl amine

The crude isocyanate from example 1, step 3 was treated with 1 equiv. benzyl alcohol and triethylamine in THF at reflux for 18 h under $N_2$. The product slowly crystallizes and is recovered by concentrating the cooled reaction mixture, diluting with ice cold aqueous acetic acid and suction filtration. Recrystallization from $CH_2Cl_2$-hexane gives the title urethane, mp 139°–140°.

The above urethane phthalimide was treated with 1 equiv anhydrous hydrazine in isopropanol for 18 h at room temperature followed by 4 h reflux. The mixture was concentrated, diluted with cold aqueous acetic acid and filtered to remove phthalazinedione. The aqueous layer was basified with NaOH followed by extraction with ethyl acetate, drying, and evaporation to afford the desired product as a solid. mp 118–121

EXAMPLE 15

Preparation of trans-4-Amino-cyclohexylmethyl N -(3,3-dicyclohexyl-1-oxo-propan-1-yl)-L-proline amide.

In a manner similar to that used in example 9, but substituting 3,3-dicyclohexylpropionic acid for 3,3-diphenylpropionic acid, the protected dicyclohexyl analog was prepared. Removal of the BOC group with HCl gas in cold EtOAc followed by trituration with Et$_2$O and filtration provided the desired product as a white solid, MP=104°–107° C. High Res. FAB MS: M+theo.= 446.37465, obs.=446.37430. Anal. ($C_{27}H_{47}N_3O_2.HCl.0.35\ H_2O$) C,H,N.

EXAMPLE 16

Preparation of trans-4-Amino-cyclohexyl]-methyl N-3-(R) or (S) phenyl-3-cyclohexyl-1-oxo-propan-1-yl)-L-proline amide.

In a manner similar to that described in example 16, but substituting 3-(R,S)-cycloxeyl-3-(R,S)-phenyl-propionic acid for 3,3-dicyclohexylpropionic acid, was 3-cyclohexyl-3-phenyl compound was prepared as a mixture of diastereomers. The diastereomers were separated via reverse phase prep LC to provide after lyophilization each diastereomer as a white fluffy solid. More polar diastereomer MP=116°–119° C., FAB MS: M+=440; contains approx. 7% of the other diastereomer by 400 MHz NMR. Anal.($C_{27}H_{41}N_3O_2.1.25TFA.0.80\ H_2O$) C,H,N. Less polar diastereomer MP=120°–122° C., FAB MS: M+=440; contains approx. 4% of the other diastereomer by 400 MHz NMR. Anal.($C_{27}H_{41}N_3O_2.1.25TFA.0.65H_2O$) C,H,N.

EXAMPLE 17

Preparation of trans-4-Aminocyclohexylmethyl L- and D-3, 3-Dicyclohexylalanyl-L-proline amide.

Step 1

Preparation of N-CBZ-D,L-3,3-dicyclohexylalanine.

A solution of 2.00 g of D,L-3,3-diphenylalanine HCl in 50 ml acetic acid/10 ml $H_2O$ was hydrogenated at 62 psi on a Parr apparatus over 500 mg of Ir black catalyst. After 24 h, a second portion of catalyst was added and the reaction continued for a second 24 h interval. The reaction was filtered through a Celite pad, and the filtrate concentrated in vacuo to give a tan foam. The foam was diluted with Et$_2$O, scraped, and sonicated to give 1.38 g of D,L-3,3-dicyclohexylalanine HCl as a tan solid, MP=261°–264° C. The amino acid (4.76 mmol) was dissolved in 40 ml of 2N NaOH, and the solution cooled to 0° C. The solution was treated dropwise with 1.06 g(6.19 mmol) of benzyl chloroformate with the temp. maintained at <5° C. After completion of the addition, the reaction was stirred at 0° C. for 15 min., then at room temp. for 1 h. The suspension was acidified to pH 2 with 2.75M KHSO$_4$ solution, and the suspension extracted with 3×50 ml of EtOAc. The combined extracts were dried, decolorized with activated carbon, and filtered through a Celite pad. Concentration provided a peach colored oil which partially crystallized on pumping. The residue was triturated with hexanes which induced further crystallization. Filtration provided 1.00 g (55%) of desired product as a white crystalline solid, MP=150°–152° C. High Res. FABMS: M+theo.=388.24878; obs.= 388.24793.

Step 2

Preparation of N-CBZ-L- and D-3,3-Dicyclohexylalanyl-L-proline.

A solution of 850 mg (2.19 mmol) of N-CBZ-D,L-3,3-dicyclohexylalanine, 363 mg (2.19 mmol) of proline methyl ester HCl 325 mg (2.41 mmol) of EDC, and 488 mg (4.82 mmol) of triethylamine in 12 ml of anh. DMF was treated with 462 mg (2.41 mmol) of EDC, and the resulting solution stirred at room temp. in an N$_2$ atmosphere for 18 h. The reaction was diluted with 3× its volume of 10% citric acid solution, and the suspension extracted with 2×40 ml of EtOAc. The combined EtOAc extracts were washed with water and brine, and were dried and concentrated to provide the crude coupling product. The crude product was purified via column chromatography over silica gel with 2.5% MeOH/CHCl$_3$ to give the pure coupling product as a white foam. The foam was dissolved in 5 ml 2M LiOH/5 ml DME, and the solution stirred vigorously at room temp. for 18 h. The reaction was acidified with 10% citric acid solution and extracted with EtOAc. The extract was washed with brine, dried, and concentrated to provide the crude N-CBZ-L- and D-3,3-dicyclohexylalanine-L-proline as a mixture of diastereomers. The acid diastereomers were separated via reversed phase preparatory HPLC to provide 370 mg of the more polar diastereomer as a white foam. High Res. FABMS: M+theo.=485.30154, obs.=485.30090. 363 mg of the less polar diastereomer was also obtained as a glass. High Res. FABMS: M+theo.=485.30154, obs.=485.30162. Each diastereomer was completely free of the other diastereomer by analytical HPLC and NMR.

Step 3

Preparation of L- and D-3,3-Dicyclohexylalanyl-L-proline-N-[trans-4-aminocyclohexyl]methyl amide.

A solution of 361 mg (0.75 mmol) of the more polar diastereomer of N-CBZ-3,3-Dicyclohexylalanyl-L-proline, 197 mg (0.75 mmol) of trans-(4-N-CBZ-aminocyclohexyl-)methyl amine, 112 mg (0.83 mmol) of HOBT, and 84 mg (0.83 mmol) of triethylamine in 5 ml anh. DMF was treated with 159 mg (0.83 mmol) of EDC, and the resulting solution stirred at room temp. in an $N_2$ atmosphere for 18 h. The reaction was diluted with 3× its volume of water, and the suspension stirred vigorously at room temp. for 15 min. The suspension was filtered, and the white solid washed with water and dried. 528 mg (97%) of the bis-CBZ protected coupling product was obtained, MP=79°–82° C. A 500 mg sample of this material was dissolved in 40 ml of 4:1 EtOH/water, and was hydrogenated on a Parr apparatus at 50 psi over 150 mg of $Pd(OH)_2$ catalyst for 18 h. The reaction was filtered through a Celite pad, and the filtrate concentrated to provide the crude product as a clear oil. The oil was purified via reverse phase prep LC to provide 330 mg of the desired product after lyophilization as an amorphous glass. HR FABMS: M+theo.=461.38555, obs.=461.38646. Anal.($C_{27}H_{48}N_4O_2$.2.40TFA.0.05$H_2$) C,H,N.

An identical procedure performed on 348 mg (0.72 mmol) of the more polar diastereomer of N-CBZ-Dicyclohexyla-lanine-L-proline provided 275 mg of product as an amorphous tacky solid. HR FABMS: M+theo.=461.38646, obs.= 361.38664. Anal. ($C_{27}H_{48}N_4O_2$.2.50TFA.0.50$H_2O$) C,H,N. This material was the more active diastereomer in a Thrombin inhibition assay, and was therefore assigned the (R)-configuration at the dicyclohexylalanine alpha position.

EXAMPLE 18

Preparation of trans-4-Aminocyclohexylmethyl N-BOC-L-and D-3,3-Dicyclohexylalanyl-L-proline amide Step 1

Preparation of N-BOC-D,L-3,3-dicyclohexylalanine.

To a solution of 2.00 g (6.90 mmol) of D,L-3,3dicyclo-hexylalanine in in 17 ml 1N NaOH/9 ml water/l 7 ml 1,4 dioxane cooled to 20° C. was added 1.66 g (7.59 mmol) of di-(t-butyl) dicarbonate in portions over approx. 2 min. The solution was stirred in the cold for 5 min., then at room temp. for an additional 2 h. The reaction was concentrated to remove most of the dioxane, and was cooled in an ice bath. The cold reaction was acidified to pH 2 with 1N $KHSO_4$, and was extracted 2× with EtOAc. The combined extracts were washed with water and brine, and were dried and concentrated to provide 2.43 g(90%) of the desired product as a white crystalline solid. MP=188.0°–189.5° C. High. Res. FABMS: M+theo.=354.26443, obs.=354.26588.

Step 2

Preparation of N-BOC-L- and D-3,3-Dicyclohexylalanyl-L-proline.

In a manner identical to the example 18, step 2, from 2.10 g (5.94 mmol) of N-BOC-D,L-3,3-dicyclohexylalanine was obtained 0.82 g of the more polar acid diastereomer as a clear oil/foam, HR FABMS M+theo.=451.31720, obs.= 451.31764. A 1.20 g quantity of the less polar diastereomer was also obtained, HR FAB MS M+theo.=45 1.31720, obs.=451.31587. Each diastereomer was free of any of the other diastereomer by analytical HPLC and NMR.

Step 3

Preparation of trans-4-Aminocyclohexylmethyl N-BOC-L-and 25 D-3,3-Dicyclohexylalanyl-L-proline amide.

In a manner identical to example 18, step 3, from 264 mg of the more polar diastereomer of N-BOC-3,3-Dicyclohexy-lalanyl-L-proline was obtained 135 mg of the desired product as a clear glass. FAB MS: M+=561.

Also in an identical manner from 370 mg of the less polar diastereomer of N-BOC-3,3-Dicyclohexylalanyl-L-proline was obtained 155 mg of desired product as a clear glass. FAB MS: M+=561. Anal.($C_{32}H_{56}N_4O_4$.0.70EtOAc.0.15$H_2O$) C,H,N.

EXAMPLE 19

Preparation of trans-4-t-butoxycarbonylaminocyclohexy-lmethyl L-proline amide

Step 1

Preparation of trans-4allyloxycarbonylaminomethyl-cyclohexanecarboxylic acid

A stirred solution of 34.2 g (217.5 mmol) of trans 4ami-nomethylcyclohexanecarboxylic acid (Aldrich) in 217 mL of 2M aq. NaOH and 217 mL of dioxane was cooled to 15° C. To this solution was added 25 mL (235 mmol) of allyl chloroformate (Aldrich) in a slow stream. After the addition, the cold bath was removed, and the solution was stirred overnight at ambient temperature. The reaction mixture was poured slowly into a rapidly stirred mixture of 1L of 1M aq. citric acid and ice. The resulting mixture was stirred for 0.5 h and the precipitate collected by filtration, washed with water, and dried to a constant weight of 49.3 g (94%) of the title compound as a colorless solid.

Step 2

Preparation of trans-4-t-butoxycarbonylaminocyclohexyl-(allyloxycarbonyl)methylamine allyloxycarbonyl)methy-lamine A stirred solution of 15.0 g (62.2 mmol) of trans-4-allyloxycarbonylaminomethylcyclohexanecarboxylic acid in 550 mL of benzene and 9.1 mL (65.3 mmol) of triethylamine was heated to 45° C under Ar. Diphenylphosphoryl azide (14.1 mL, 65.3 mmol, Aldrich) was added in one portion, and the solution stirred for 24 h at 45° C. The solution was cooled to 10° C. and 65 mL of a 1.0M solution of lithium tbutoxide in THF (Aldrich) was added such that the reaction temperature remained between 8°–10° C. A second 65 mL portion of t-butoxide solution was added, and the solution stirred for 45° C at 8°–12° C. This solution was then poured into a rapidly stirred mixture of 1M aq. citric acid and ice, and the resulting mixture stirred for 1 h. This mixture was extracted with 2 portions of ethyl acetate, the combined organic layers washed with 2×10% $Na_2CO_3$, brine, and dried over $Na_2SO_4$. This solution was poured through a pad of 150 g of silica gel, and the pad washed with 2×300 mL of ethyl acetate. Evaporation of the filtrate gave 15.9 g (82%) of the title compound as a solid.

Step 3

Preparation of trans-4-t-butoxycarbonylaminocViohexy-lmethylamine

To an Ar filled flask containing 5 g (4.33 mmol) of tetrakis(triphenylphosphine) palladium (Aldrich) and 15.92 g (50.96 mmol) of trans-4-t-butoxycarbonylaminocyclohexyl-(allyloxycarbonyl)methylamine was added 220 mL of dry THF. After the solids had dissolved, the solution was stirred for 5 min. and 50 mL (483 mmol) of diethylamine (Aldrich) was added in one portion. The solution was stirred at ambient temperature overnight. The solvents were removed by rotovap, and the residue partitioned between ice-cold 0.5M aq HCl and ethyl acetate. The organic layer was extracted with cold 0.5M aq HCl and the combined aqueous layers washed with ethyl acetate, basified with aq NaOH and extracted with 3× ethyl acetate. The combined organic layers were washed with water, brine, dried over $Na_2SO_4$ and solvents removed to give an oil that was chromatographed on 250 g of fine $SiO_2$ using 90:10:1 chloroform-methanol-ammonium hydroxide to give 7.9 g (56%) of the title compound as a colorless semi-solid: NMR (CDCl3) d 0.5–1.5 (m,4H), 1.8–1.3 (m,1H), 1.44 (s,9H), 1.81 (dm,J=10.3, 2H), 2.03 (dm,J=10.3, 2H), 2.53 (d,J=6.6, 2H), 3.37 (br s,1H), 4.44 (br s,1H).

Step 4

Preparation of trans-4-t-butoxycarbonylaminocyclohexylmethyl L-proline amide

To a stirred solution of 1.70 g (6.8 mmol) of Cbz-L-proline (Bachem), 1.54 g (6.74 mmol) of trans-4-t-butoxycarbonylaminocyclohexylmethylamine, and 919 mg (6.8 mmol) of 1-hydroxybenzotriazole hydrate (Aldrich) in 11 mL of DMF under Ar was added 1.30 g (6.8 mmol) of EDC and 1.90 mL (13.6 mmol) of triethylamine. The solution was stirred at ambient temperature overnight. The solvents were removed by rotovap and the residue partitioned between $CHCl_3$ and 1M aq citric acid. the aqueous layer was extracted with $CHCl_3$ and the combined organic layers were washed with 10% $Na_2CO_3$, dried over $MgSO_4$ and the solvents removed to give 3.0 g of a glassy foam. A flask containing a solution of this material in 150 mL of absolute ethanol and 1.5 mL of acetic acid was treated with 1 g of 10% palladium on carbon and fitted with a balloon filled with hydrogen. After stirring for 7.5 h, the mixture was degassed and filtered to give a solution that was concentrated by rotovap. The resulting residue was partitioned between $CHCl_3$ and cold 1M aq NaOH. The organic layer was washed with water, dried over $Na_2SO_4$ and solvents removed to give a semi-solid that was chromatographed on 100 g fine $SiO_2$ using 93:7:0.7 chloroform-methanol-ammonium hydroxide to afford 1.05 g of the title compound as a colorless solid: NMR (CDl_3) d 0.96–1.14 (m,4H), 1.44 (s,9H), 1.66–1.82 (m,4H), 1.83–2.06 (m,5H), 2.06–2.19 (m,1H), 2.83–2.93 (m, 1H), 2.93–3.15 (m,3H), 3.38 (br s,1H), 3.72 (dd, J=9.1, 5.3, 1H), 4.01 (br s,1H), 7.73 (br s,1H).

EXAMPLE 21

Preparation of trans-4-Aminocyclohexylmethyl N-2-cyclohexyethyl-3-cyclohexyl-D-alanyl-L-proline amide dihydrochloride salt:

Step 1

Preparation of trans-4-Aminocyclohexylmethyl N-2-phenylethyl-3-cyclohexyl-D-alanyl-L-proline amide To a stirred mixture of 241 mg (0.503 mmol) of trans-4-aminocyclohexylmethyl 3-cyclohexyl-D-alanyl-L-proline amide, 65 μL (0.554 mmol) of phenylacetaldehyde (Aldrich), and 102 mg (3.78 mmol) of aluminum foil cut in small pieces in 13 mL of methanol was added 13.7 mg (0.05 mmol) of mercuric chloride. The mixture was stirred overnight under Ar. Filtered through a pad of Celite and washed with methanol. The filtrate was evaporated by rotovap, the residue dissolved in ethyl acetate, washed with 2× sodium potassium tartrate, brine, dried over $Na_2SO_4$ and the solvents removed to give a residue which was chromatographed on $SiO_2$ using 96:4 chloroform-methanol to give 260 mg of an oil. This oil was dissolved in 40 mL of ethyl acetate, cooled to 0° C. and saturated with HCl gas. The flask was stoppered and stirred in the cold for 0.5 h. The solution was sparged with a stream of Ar for 1 h and concentrated to give an oil which was chromatographed on $SiO_2$ using 99:1 chloroform-methanolic ammonia to give 120 mg of the title compound as a colorless solid.

EXAMPLE 22

Preparation of trans-4-Aminocyclohexylmethyl N-2-cyclohexylethyl-3-cyclohexyl-D-alanyl-L-proline amide A solution of 85 mg (0.176 mmol) of trans-4-Aminocyclohexylmethyl N-2-phenylethyl-3-cyclohexyl-D-alanyl-L-proline amide in 10 mL of ethanol and 3 mL of acetic acid was hydrogenated at 50 psi in the presence of 33 mg of platinum oxide overnight. The catalyst was removed by filtration and washed with ethanol. Concentration of the filtrate afforded a residue which was partitioned between EtOAc and 1M aq. NaOH. The organic layer was washed with water, brine, dried over $Na_2SO_4$ and the solvents removed to give 87 mg of an oil. This material was dissolved in ethyl acetate and treated with ethanolic HCl to afford the title compound as a colorless dihydrochloride salt.

EXAMPLE 23

Preparation of trans-4-Aminocyclohexylmethyl N-[3-(5H-dibenzo[a,d]-cycloheptene-5-yl)-1-yl]-L-proline amide To a stirred solution of 87.60 mg(0.35 mmol) of 5H-dibenzo[a,d]-cycloheptene-5-yl)-1-oxopropan-1-yl ]-L-proline amide To a stirred solution of 87.60 mg(0.35 mmol) of 5H-dibenzo[a,d]-cycloheptene-5-acetic acid, 125.00 mg(0.35 mmol) of trans-4-aminocyclohexylmethyl L-proline amide, 53 mg (0.39 mmol) HOBt, and 40 mg (0.39 mmol) of TEA in 2 ml of anh. DMF under an $N_2$ atmosphere was added 75 mg (0.39 mmol) of EDC. The resulting solution was stirred at room temp. for 18 h. The reaction was diluted with 3× its' volume of water, and the suspension stirred vigorously at room temp. for 20 min. Filtration and drying in vacuo provided 120 mg of the off white solid coupling product, MP=102°–105° C.

The coupling product was dissolved in 8 ml of EtOAc, and the solution was cooled to 0° C. The cold solution was bubbled with HCl gas for 3 min., capped, and stirred in the cold for approx. 30 min. The cold rxn. was purged with $N_2$, and a tacky precipitate formed. The susp. was diluted with $Et_2O$ sonicated, and allowed to settle. The liquid was decanted off, and the solid resuspended in $Et_2O$ and sonicated. The susp. was again decanted, and the solid residue placed on a vac. pump for 30 min. The solid residue was suspended in $Et_2O/CHCl_3$, the residue scraped from the sides of the flask, and the suspension stirred and filtered to provide 70 mg of the desired product as an off white solid. MP=181°–184° C. (dec.). Anal.($C_{29}H_{35}N_3O_2$.HCl.1.55 $H_2O$.0.35 $CHCl_3$), CHN. High Res. FAB MS: M+1theo.= 458.28075, obs.=458.28011.

EXAMPLE 24

Preparation of trans-4-Aminocyclohexylmethyl N-[3-(10,11-dihydro-5H-dibenzo[a,d]-cycloheptene-5-yl)-1-oxopropan-1-yl]-L-proline amide.

To a stirred solution of 129 mg (0.52 mmol) of 10,11-dihydro-5H-dibenzo[a,d]-cycloheptene-5-acetic acid, 180 mg (0.52 mmol) of trans-4-aminocyclohexylmethyl L-proline amide, 76 mg (0.56 mmol) HOBt, and 57 mg (0.56 mmol) of TEA in 3 ml of anh. DMF under an $N_2$ atmosphere was added 107 mg (0.56 mmol) of EDC. The resulting solution was stirred at room temp. for 18 h. The reaction was diluted with 3× its' volume of water, and the suspension stirred vigorously at room temp. for 20 min. Filtration and drying in vacuo provided an of off white solid which became quite tacky. The tacky oil/solid was dissolved in EtOAc, dried, filtered, and the filtrate conc. to give 138 mg of coupling product as a white foam.

The coupling product was dissolved in 8 ml of EtOAc, and the solution was cooled to 0° C. The cold solution was bubbled with HCl gas for 3 min., capped, and stirred in the cold for approx. 30 min. The cold rxn. was purged with $N_2$, and a tacky precipitate formed. The material was filtered off, but became extremely tacky despite numerous crystallization attempts. The material was dissolved in EtOAc, dried filtered and reisolated as a crude foam. Reverse phase prep LC provided 75 mg of the pure product as an amorphous white solid after lyophilization. Anal.($C_{29}H_{37}H_3O_2$.1.60TFA.0.20$H_2O$), CHN. High Res. FAB MS: M+1 theo.=460.29640, obs.=460.29665.

EXAMPLE 25

Preparation of trans-4-Aminocyclohexylmethyl 9-hydroxyfluorene-9-carboxy-L-proline amide.

9-Hydroxyfluorene-9-carboxylic acid (251 mg., 1.11 mmole) and trans-4-(tert-butoxycarbonyl-amino)cyclohexylmethyl L-proline amide (300 mg., 0.266 mmole) were dissolved in 15 ml of dimethyl acetamide, followed by addition of 170 mg. (1.11 mmole) of HOBt and 256 mg. (1.33 mmole) of EDC, and adjustment to pH 8 with NMM. The reaction was monitored to completion via TLC, then concentrated in vacuo, and extractive workup with EtOAc yielded 495 mg of crude Boc protected material. This product was dissolved in 10 ml. of 1:1 TFA-$CH_2Cl_2$, let 20 min., and the TFA was removed under reduced pressure and the product purified by preparative HPLC using a TFA(0.1%)-$CH_3CN$ gradient. Lyophilization of pure fractions gave the title compound as a trifluoroacetic acid hydrate salt: $C_{26}H_{31}N_3O_3.CF_3COOH.H_2O$ (FAB MS 434 (M+H) and 416 (M+H—$H_2O$).

In Vitro Assay For Determining Proteinase Inhibition

Assays of human a-thrombin and bovine trypsin were performed at 25° C. in 0.05M TRIS buffer pH 7.4, 0.15M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human a-thrombin ($K_m$=125 μM) and bovine trypsin ($K_m$=125 μM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i - 1 = [I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

In Vivo Studies To Measure Thombotic Occlusions

Applicants have conducted in vivo studies of the compounds claimed herein using the following rat ferric chloride assay.

In the assay used to determine in vivo activity of the thrombin inhibitors or the invention, Male Sprague-Dawley rats (body weights 200–350 grams) were anesthetized with dial-urethane solution (0.1 ml/100 gm body weight i.p.), and a lateral tail vein was cannulated with a 23 gauge needle connected to a 12 inch length of PE50 tubing. The tubing was attached to a 3-way valve by a tubing adapter. Saline (control) or test compound, as appropriate, was administered via the tail vein catheter. A tracheostomy was performed with a 0.75 inch length of PE205 tubing. The right carotid artery was exposed and a 1.3 mm diameter Doppler flow probe was placed on the vessel. Body temperature was maintained at 37° C. using a heat lamp.

Rats (8–10/group) were randomized to continuous intravenous infusions of saline or test compound administered via the tail vein at a rate of 0.028 ml/min. Treatment infusions were initiated 60 min before the placement of a 3 mm square piece of Whatman No. 1 filter paper saturated with 35% $FeCl_3$ onto the exposed carotid artery distal to the flow probe. Treatment infusions were continued for an additional 90 minutes after the application of $FeCl_3$ (total infusion duration 150 minutes) if thrombotic occlusions did not occur, or were terminated 30 minutes after thrombotic occlusion of the vessel. Time to occlusion was defined as the time from application of FeCl₃ to thrombotic occlusion of the vessel. At the termination of the study (90 minutes after application of FeCl₃ in animals which did not occlude, or at 30 minutes after thrombotic occlusion), 3 ml blood samples were drawn by cardiac puncture into 0.3 ml of 3.8% sodium citrate.

The results show that compounds of the invention prevent thrombotic occulsions.

Thrombin Inhibitors—Therapeutic Uses

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carders to which the compound molecules are coupled. The thrombin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.1 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carders (collectively referred to herein as "carder" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, nontoxic, pharmaceutically acceptable, inert carder such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carder such as ethanol, glycerol, water and the like. Moreover, when desired or necessary, suitable binders, lubricants, distinegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfafin.

What is claimed is:

1. A compound having the formula:

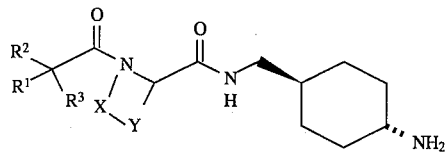

wherein $R^1$ and $R^2$ are independently
  hydrogen,
  phenyl,
  naphthyl,
  biphenyl,
a 5- to 7- membered mono- bicyclic heterocyclic ring or bicyclic heterocyclic ring system any ring of which may be saturated or unsaturated, and which consists of carbon atoms and from one to three heteroatoms selected from the group consisting of N, O and S,
  $C_{1-4}$ alkyl,
  branched $C_{1-4}$ alkyl,
  $C_{3-7}$ cycloalkyl,
  $C_{5-12}$ bicylic alkyl,
  $C_{11-16}$ tricylic alkyl,
  $(CH_2)_n R^4$,
  $CH(R^4)_2$, wherein $R^4$ is the same or different,
  $CH(R^4)(OR^4)$, $(CH_2)_n OR^4$, or $R^2$ may be joined with $R^1$ to form a four- to seven membered carbon ring in which zero to two carbon atoms may be substituted with heteroatoms independently selected from the list N, O, and S, where n is 1, 2, 3 or 4;

$R^3$ is
  H,
  $N(R^1)_2$, wherein $R^1$ is the same or different,
  $R^1 OCONH$,
  $R^1 CONH$,
  $(CH_2)_p OH$, where p is 0, 1, 2, 3 or 4,
  $R^1 SO_2 NH$, or
  $(R^1)_m NCONH$, where m is 1 or 2, wherein $R^1$ is the same or different;

$R^4$ is
  phenyl,
  naphthyl,
  biphenyl,
a 5- to 7- membered mono- or bicyclic heterocyclic ring or bicyclic heterocyclic ring system any ring of which may be saturated or unsaturated, and which consists of carbon atoms and from one to three heteroatoms selected from the group consisting of N, O and S,
  $C_{1-4}$ alkyl,
  branched $C_{1-4}$ alkyl,
  $C_{3-7}$ cycloalkyl,
  $C_{5-12}$ bicyclic alkyl, or
  $C_{11-16}$ tricyclic alkyl;

X is $(CH_2)_q$ where q is 2; and

Y is $(CH_2)_r$ where is 1.

2. A compound of claim 1 selected from the group consisting of:

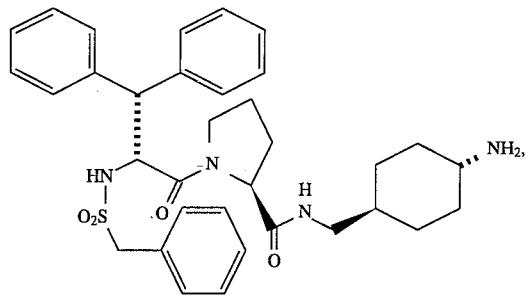

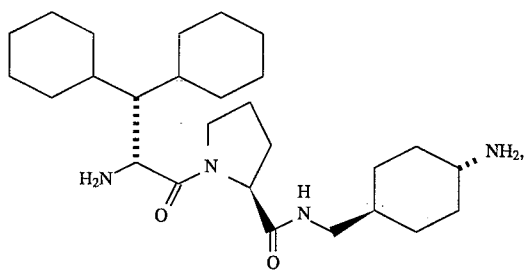

-continued
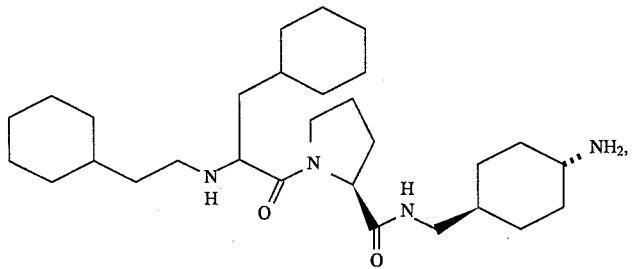
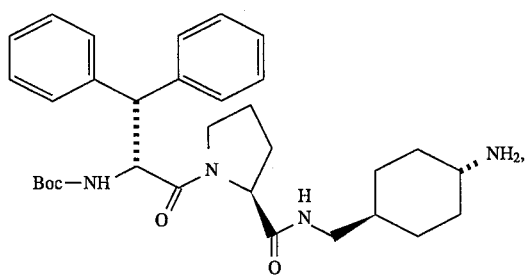
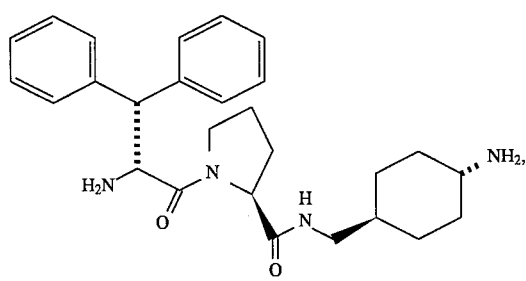
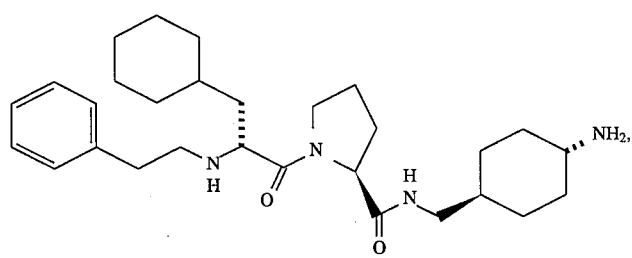
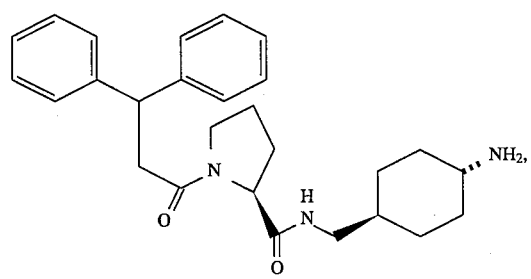
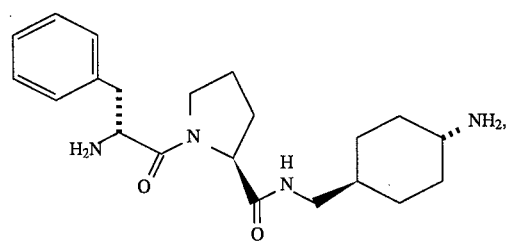

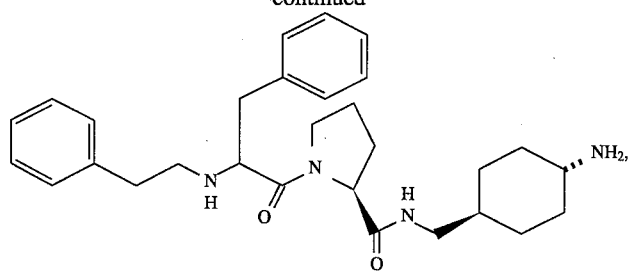
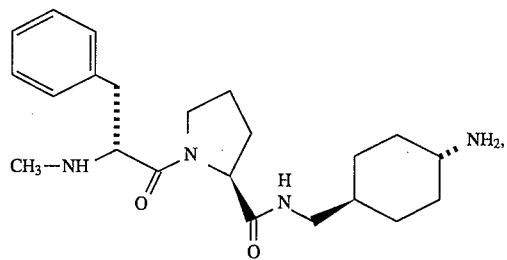
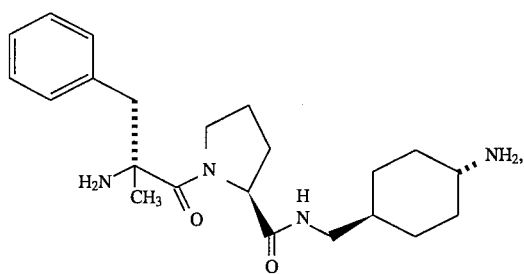
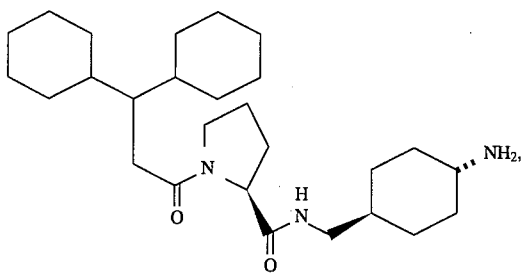
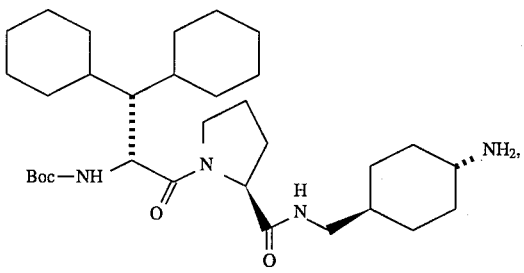
3. A composition for inhibiting thrombin blood comprising a compound of claim 1 and a pharmaceutically acceptable carrier.
4. A method for inhibiting thrombin in blood comprising adding to the blood a composition of claim 3.
5. A compound selected from the group consisting of

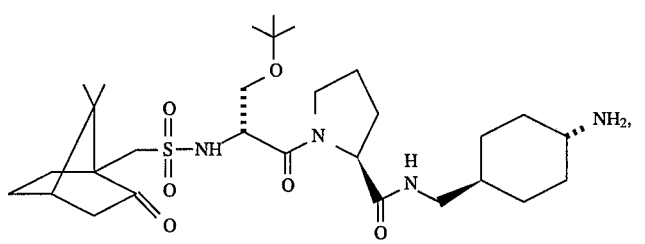
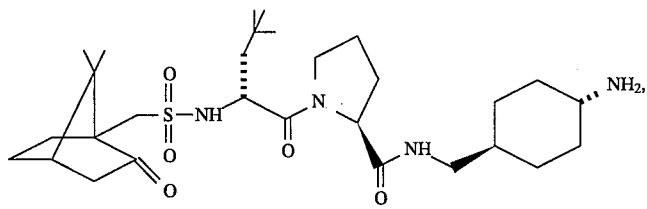
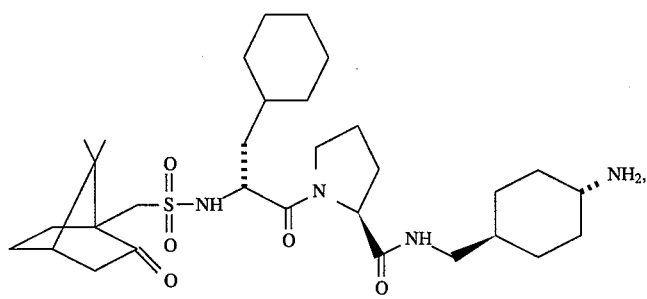
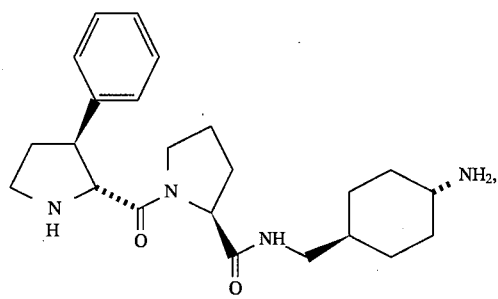
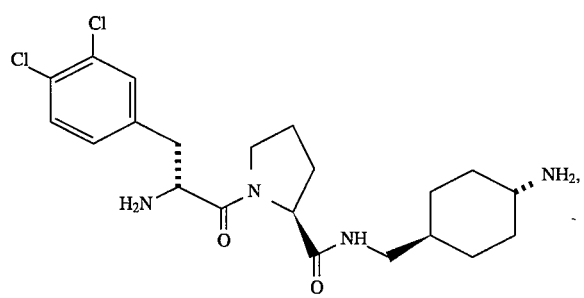
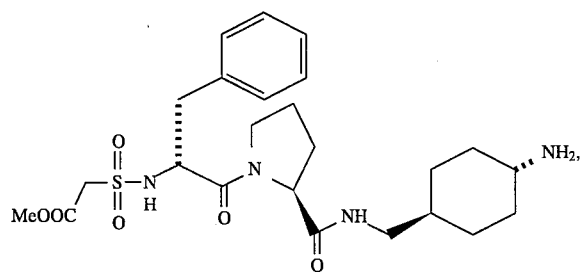

-continued
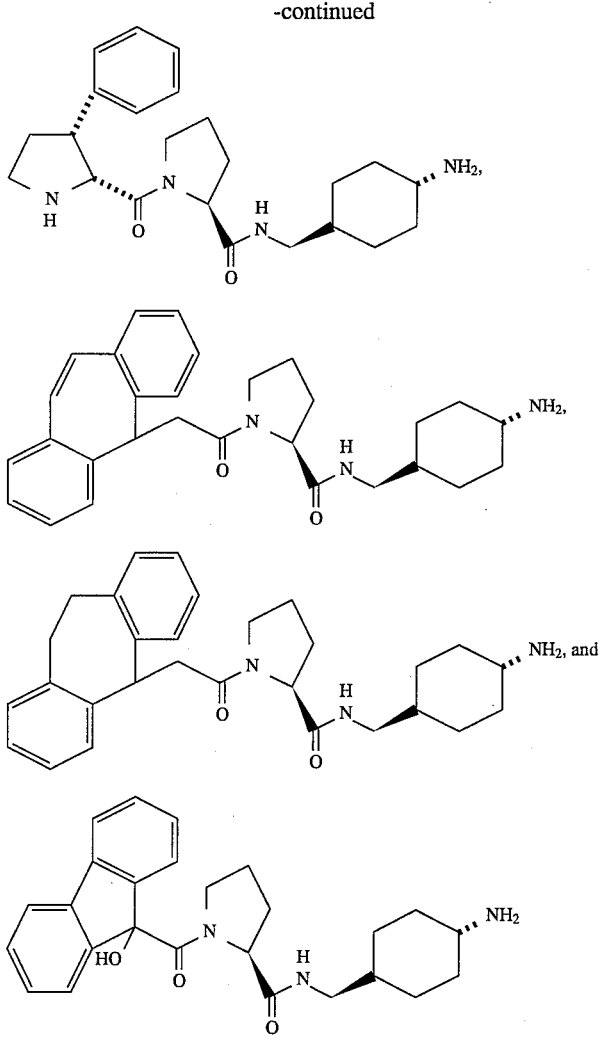
and pharmaceutically acceptable salts thereof.